United States Patent
Buckley

[11] Patent Number: 5,109,869
[45] Date of Patent: May 5, 1992

[54] DISPOSABLE UTERINE SOUND DEVICE

[75] Inventor: Mary E. Buckley, Sherman Oaks, Calif.

[73] Assignee: Baxter International Inc., Deerfield, Ill.

[21] Appl. No.: 643,970

[22] Filed: Jan. 22, 1991

[51] Int. Cl.⁵ .............................. A61B 5/103
[52] U.S. Cl. ..................... 128/778; 606/190; 33/512
[58] Field of Search ............. 128/774, 778, 777; 606/60, 76, 190; 33/511, 512

[56] References Cited

U.S. PATENT DOCUMENTS

| | | | |
|---|---|---|---|
| D. 265,342 | 7/1982 | Glassman | D24/23 |
| 672,377 | 4/1901 | Kearns . | |
| 3,196,876 | 7/1965 | Miller | 128/343 |
| 3,587,588 | 6/1971 | Murr | 128/341 |
| 3,809,091 | 5/1974 | Shute | 606/190 |
| 3,938,504 | 2/1976 | Dickinson, III et al. . | |
| 3,994,301 | 11/1976 | Agris | 606/190 |
| 4,016,867 | 4/1977 | King et al. . | |
| 4,121,572 | 10/1978 | Krzeminski . | |
| 4,224,951 | 9/1930 | Hasson | 128/778 |
| 4,362,167 | 12/1982 | Nicolai et al. | 128/778 |
| 4,489,732 | 12/1984 | Hasson | 128/778 |
| 4,664,114 | 5/1987 | Ghodsian | 604/101 |
| 4,685,474 | 8/1987 | Kurz et al. | 33/512 |
| 4,959,067 | 9/1990 | Muller | 606/190 |

Primary Examiner—Max Hindenburg
Attorney, Agent, or Firm—Kay H. Pierce; Paul C. Flattery

[57] ABSTRACT

A disposable uterine sound device is described for measuring the depth and course of an uterine cavity. The device is formed by coating a copper rod and a portion of an attached nylon handle with polyvinyl chloride. The coating is then printed with a generally nonleachable biocompatible ink to form graduations indicating units of measure of length. The resulting device is a flexible, smooth service device which minimizes trauma to a patient during use.

14 Claims, 1 Drawing Sheet

DISPOSABLE UTERINE SOUND DEVICE

BACKGROUND OF THE INVENTION

The present invention relates generally to uterine sound devices for measuring the depth and course of a uterus and more specifically relates to flexible, disposable, polyvinyl chloride-coated uterine sound devices.

In the gynecological field, it is sometimes necessary for a physician to measure the internal cavity of a uterus. For instance, such measurements may be necessary to ascertain the depth and course of an uterine cavity to prevent the accidental perforation of the uterus during a subsequent surgical procedure. In some instances such measurements may be performed both before and after a surgical procedure to insure that the uterus has properly contracted upon completion of a procedure.

Most uterine sound devices that are currently in use are reusable devices. Generally, these devices are silver-plated copper rods with graduations engraved in the surface of the rod to indicate units of length along the rod. Such devices have several disadvantages. For instance, since the devices are formed by plating silver onto copper, the resulting silver plating may gradually wear off leaving the copper exposed to the patient as the devices are repeatedly reused. This is a disadvantage because the copper can be potentially harmful to the patient. Thus, it is necessary for medical personnel to continuously monitor such devices to be sure that the silver-plating is still intact. Also, silver-plated uterine sound devices have the disadvantage that medical personnel must be careful when cleaning the devices to prevent the accidental removal of the silver plating.

Another disadvantage of such sound devices is the fact that by engraving the graduations on to the device, the engraved portions of the device can exacerbate trauma to the patient as the device is introduced into the cervix. In fact, in the past, such indentions have been intentionally used to collect blood as the sound device is removed to provide the physician a point of reference on the surface of the sound to determine the depth of the uterus.

While some reusable sound devices have a degree of flexibility and malleability, it is desired to provide a device which has greater flexibility and malleability than the currently available products. Flexibility is important because it can reduce the possibility of accidental perforation of the uterus as a physician reaches the uterine wall. A degree of flexibility is a desirable feature because it allows the sound device to flex slightly when the wall of the uterus is reached thereby putting the physician on notice that further pressure may cause a perforation. Malleability of a uterine sound device is a desirable feature because it also prevents the possibility of accidental perforation. Typically, before a sound device is inserted, the physician has performed a pelvic examination to determine if the uterus is anteverted, retroverted or in any other position. If the sound device is sufficiently malleable, the physician may then bend the device so that it generally conforms to the presumed course of the uterine cavity. Thus, as the device is inserted, it is more likely to follow the natural course of the uterine cavity and it is consequently less likely to perforate the uterine wall. If the sound device is too flexible or too malleable, it may not be able to maintain its desirable shape during insertion which will limit a physician's ability to accurately assess the position of the sound within the uterine cavity.

Disposable uterine sound devices have also been used in the past. Generally, these devices are made entirely of plastic. These devices are similar to the non-disposable uterine sound devices in that the graduations are imprinted onto the device. Thus, the outer surface of the device can still induce unnecessary trauma to a patient during insertion and removal. In some disposable uterine sound devices, flexibility has been created by producing a series of notches in the devices to allow the devices to bend. While these notches provide flexibility, they are disadvantageous in that they can also cause unnecessary trauma and limit the ability of the device to maintain its shape after it has been bent.

SUMMARY OF THE INVENTION

In view of the disadvantages of the currently available disposable and reusable uterine sound devices, it is an object of this invention to provide a disposable device which is sufficiently flexible and appropriately malleable. It is also an object of the present invention to provide a sound device that has a relatively smooth surface to minimize patient trauma. Finally, it is an object to provide a device that can be easily manufactured and sterilized using a variety of techniques at a reasonable cost. These and other objects of the invention have been met by the device described herein below.

The subject device can be briefly described as a uterine sound device for measuring the depth and course of a uterine cavity. The device includes a handle and a shaft attached to the handle. The shaft has a inner metallic core and an outer plastic coating.

DETAILED DESCRIPTION OF THE PREFERRED EMBODIMENT

Figure 1:
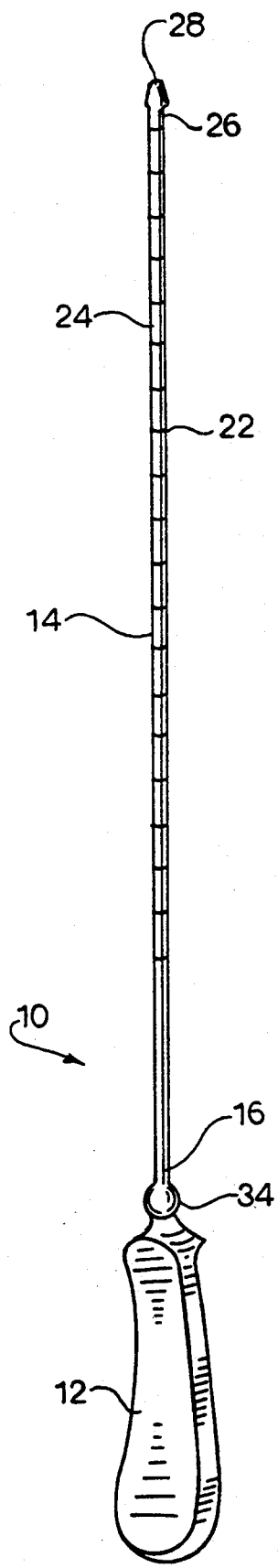
FIG. 1 is a perspective view of the invention.
Figure 2:
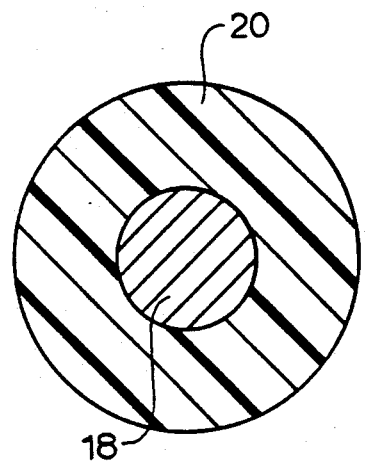
FIG. 2 is a cross-sectional view of a shaft of the device.

Refer now to FIG. 1 which is a perspective view of the subject invention. The device 10 includes a handle 12 and a shaft 14. The shaft is attached to the handle at the proximal end 16 of the shaft 14. The shaft includes an inner metallic core 18 and an outer plastic coating 20 as illustrated in FIG. 2. The core may be formed of a variety of metals or metal alloys. For instance, the core may be formed using copper, silver, gold, aluminum, nickel, platinum, iron, tin and alloys thereof. However, in the preferred embodiment, the core is formed of copper. Copper is the preferred metal because it is inexpensive and has the desired flexibility and malleability characteristics. Further, it possesses desired thermal properties which facilitate manufacturing. Each of these characteristics will be discussed in great detail below.

The coating 20 may be formed of a variety of plastic or synthetic polymers. In the preferred embodiment, a polyvinyl chloride polymer is used. However, in other embodiments, the polymer may be selected from the group consisting of polypropyline, polyethylene, polystyrene, polybutidine, polyamide, and polyoleofin. Generally, any synthetic polymer may be used provided it is biocompatible with human tissue. In other words, it is important that the coating does not irritate or otherwise harm a patient when the patient's tissue comes in contact with the coating. Other required characteristics of the coating in the preferred embodiment of the invention are that it is capable of being used in a dipping process and that it is compatible with a printing process as discussed below. It is also necessary that the coating material be flexible in its solid phase and not be subject to chipping, cracking, tearing and splitting as the sound device is used or sterilized.

One desirable characteristic of the material chosen to provide the coating is that it be sufficiently smooth to minimize trauma to a patient, yet possess surface characteristics that are compatible with a printing process as discussed below.

In the preferred embodiment of the invention, the shaft 14 includes a series of printed graduations 22 to indicate units of measure along the length of the shaft 14. The graduations are printed rather than engraved on the shaft 14 to provide a smooth outer surface 24. This smooth outer surface reduced trauma which may occur when using a sound device having engraved or indented graduations on its outer surface 24.

A variety of inks may be used to produce the graduations 22. Generally, any ink may be used provided it is nonleachable and biocompatible. The use of printed graduations rather than engraved graduations creates a significant advantage of the present invention over prior-art devices. Printed graduations are much easier to read than engraved graduations and thus allow a physician to determine the depth of the uterus by reading the graduations while the sound is actually inserted in the patient rather than requiring the physician to withdraw the sound in order to make a reading. Since the physician is easily able to determine how much of the sound is inserted in the uterus at any given time, it is less likely for a physician to accidentally over insert the sound thereby causing an accidental perforation.

As discussed above in the background of the invention, it is desirable that the shaft 14 has a degree of flexibility. A test has been developed to measure the flexibility of a shaft 14. The test involves placing a handle 12 of a finished device in a fixture such that the distal 26 end is generally perpendicular to a fixed surface. The device is moved toward the fixed surface at a fixed, predetermined speed until the distal end 26 contacts the fixed surface and the shaft 14 begins to flex. At the instance of flexure of the shaft 14, the force required to cause the shaft to flex is measured. This force is directly related to the flexibility of the shaft and can be used as a test of acceptability of the device.

In the preferred embodiment of the invention, the proximal end 26 of the shaft 14 includes an enlarged tip 28. The purpose of the tip is to reduce the possibility of accidental perforation of the uterine wall. Generally speaking, the relative diameter of the tip 28 as compared to the diameter of the shaft 14 is on the order of a ratio of 5:4. For instance, if the diameter of the shaft is 0.12", the diameter of the tip may be on the order of 0.15".

Figure 3:
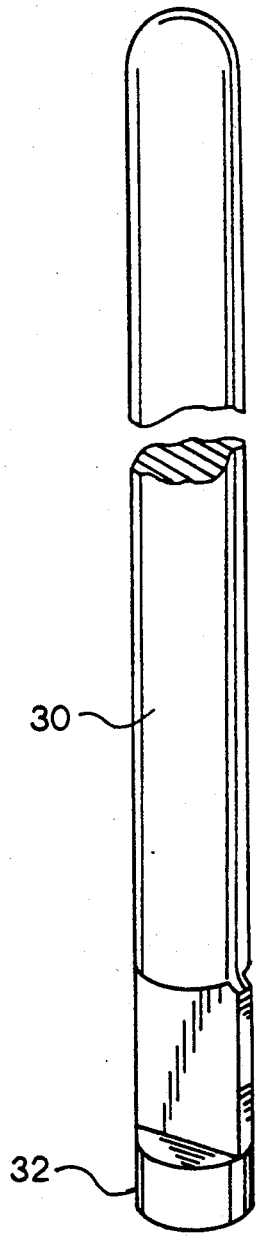
FIG. 3 is a perspective view of a rod used in the preferred embodiment of the invention.

One advantage of the preferred embodiment of the invention is that it can be manufactured using inexpensive techniques. This allows the device to be a disposable device. In the preferred embodiment of the invention, the device is manufactured using the steps described below. First, a metallic rod 30 is stamped at one end 32 to produce a flattened surface as illustrated in FIG. 3. This end 32 becomes the proximal end 16 of the shaft 14. A nylon handle 12 is then attached to the shaft by the process of insert injection molding. Nylon is used in the preferred embodiment of the invention to form the handle due to its thermal characteristics, as will be discussed below.

In the preferred embodiment, after the nylon handle 12 has been attached to the shaft 14, a tip may be formed on the distal end of the shaft. It is preferred to use the double dipped process described below to form the tip, however, other processes may be used. In the preferred embodiment of the invention, the tip is formed by initially dipping only the distal end 26 in the liquid phase of a material which will form the coating over the shaft. The end is then allowed to solidify. Next, the entire shaft and a portion 34 of the handle adjacent to the shaft is dipped in the coating material in its liquid phase. The coating is allowed to solidify over the shaft 14 and the portion 34 of the handle 12. Since a portion of the handle 12 is being subjected to a dipping process, it is necessary for the handle to maintain its integrity during the dipping process. Thus, the thermal characteristics of the material used to form the handle are important. It has been determined that nylon is an acceptable material to form the handle when polyvinyl chloride is used as the material to form the coating.

Other methods of forming a tip on the distal end 26 of the shaft include placing a cap of material over the end 26 of the shaft prior to dipping the shaft and a portion 34 of the handle 12. This cap is preferably made from the same material that is used to form the coating. However, in other embodiments, other materials may be used to form the cap. Another means by which the tip 28 may be formed is to form a bulb at the end of the metallic rod by rolling or machining the rod 18 prior to dipping.

After the coating has solidified, the graduations 22 are printed on the shaft 14. In the preferred embodiment of the invention, the graduations are placed on the shaft using a pad printing process. In other embodiments of the invention, other printing processes such as ink jet printing or laser printing may be used.

While the invention has been described in detail and with reference to specific embodiments thereof, it will be apparent for those skilled in the art that various changes and modifications can be made therein without departing from the spirit and scope of the invention.

I claim:

1. A disposable uterine sound device for measuring the depth and course of a uterine cavity, comprising:
   a handle;
   a shaft permanently attached to said handle, said shaft having a solid inner flexible metallic core; and
   an outer plastic coating covering all of said inner core and a portion of said handle.

2. A uterine sound device as recited in claim 1 wherein:
   said core is formed from a metal selected from the group consisting of copper, silver, gold, aluminum, nickel, platinum, iron, tin and alloys thereof.

3. A uterine sound device as recited in claim 1 wherein:
   said core is formed from a metal selected from the group consisting of copper, aluminum and nickel and alloys thereof.

4. A uterine sound device as recited in claim 1 wherein:
   said core is formed from copper.

5. A uterine sound device as recited in claim 1 wherein:

said coating is formed from a synthetic polymer.

6. A uterine sound device as recited in claim 1 wherein:
said coating is formed from a polyvinyl chloride polymer.

7. A uterine sound device as recited in claim 1 wherein:
said coating is formed from a polymer selected from the group consisting of polypropyline, polyethylene, polystyrene, polybutidine, polyamide, and polyoleofin.

8. A uterine sound device as recited in claim 1 further comprising:
printed graduations on said coating to indicate units of measure along the length of said shaft.

9. A uterine sound device as recited in claim 8 wherein said printed graduations are formed from a biocompatible material.

10. A uterine sound device as recited in claim 9 wherein said printed graduations are formed from generally nonleachable material.

11. A disposable uterine sound device for measuring the depth and course of a uterine cavity, comprising:
a handle;
a shaft permanently attached to said handle, said shaft having a solid inner flexible metallic core; and
an outer dipped plastic coating covering all of said inner core and a portion of said handle.

12. A uterine sound device as recited in 11 wherein said inner core is formed of copper and said dipped plastic coating is formed of polyvinyl chloride and said sound further includes printed graduations on said dipped coating to indicate units of measure along the length of said shaft.

13. A disposable uterine sound device for measuring the depth and course of a uterine cavity, comprising:
a handle;
a shaft permanently attached to said handle, said shaft having a solid inner flexible metallic core;
an outer plastic coating covering all of said inner core and a portion of said handle; and
printed graduations on said dipped coating to indicate units of measure along the length of said shaft.

14. A disposable uterine sound device for measuring the depth and course of a uterine cavity, comprising:
a nylon handle;
a shaft permanently attached to said handle, said shaft having a solid inner flexible copper core; and
an outer plastic coating covering all of said core and a portion of said handle.

* * * * *